(12) United States Patent
Chen et al.

(10) Patent No.: US 12,199,135 B2
(45) Date of Patent: Jan. 14, 2025

(54) DISPLAY DEVICE AND ELECTRONIC DEVICE

(71) Applicant: HKC Corporation Limited, Guangdong (CN)

(72) Inventors: Qinglin Chen, Guangdong (CN); Baohong Kang, Guangdong (CN)

(73) Assignee: HKC CORPORATION LIMITED, Guangdong (CN)

( * ) Notice: Subject to any disclaimer, the term of this patent is extended or adjusted under 35 U.S.C. 154(b) by 0 days.

(21) Appl. No.: 18/507,300

(22) Filed: Nov. 13, 2023

(65) Prior Publication Data
US 2024/0321934 A1    Sep. 26, 2024

(30) Foreign Application Priority Data
Mar. 23, 2023    (CN) .......................... 202310287264.9

(51) Int. Cl.
| | |
|---|---|
| G06F 3/041 | (2006.01) |
| A61L 2/10 | (2006.01) |
| F21S 4/20 | (2016.01) |
| G09F 9/30 | (2006.01) |

(Continued)

(52) U.S. Cl.
CPC .............. *H01L 27/156* (2013.01); *A61L 2/10* (2013.01); *H01L 25/167* (2013.01)

(58) Field of Classification Search
None
See application file for complete search history.

(56) References Cited

U.S. PATENT DOCUMENTS

| | | | |
|---|---|---|---|
| 9,233,179 B2 * | 1/2016 | Ranta | G06F 1/1607 |
| 10,596,281 B1 * | 3/2020 | Tchon | H05B 47/16 |

(Continued)

FOREIGN PATENT DOCUMENTS

| | | |
|---|---|---|
| CN | 103775919 A | 5/2014 |
| CN | 112416182 A | 2/2021 |

(Continued)

OTHER PUBLICATIONS

CN First Office Action dated May 31, 2023 issued in CN 202310287264.9.

(Continued)

*Primary Examiner* — Robert K Carpenter
(74) *Attorney, Agent, or Firm* — Scully, Scott, Murphy & Presser, P.C.

(57) ABSTRACT

A display device and an electronic device are provided. The display device includes a back plate, a display panel, an optical film, a first light-emitting unit, and a second light-emitting unit. The display panel and the second light-emitting unit are carried on the back plate. The optical film and the first light-emitting unit located on one side of the optical film away from the display panel are accommodated in an accommodating cavity cooperatively defined by the display panel and the back plate. The visible light emitted by the first light-emitting unit is incident on the display panel via the optical film. A part of the ultraviolet light emitted by the second light-emitting unit avoids the display screen and is emitted onto the transparent cover plate, and another part of the ultraviolet light is emitted onto the transparent cover plate via the display screen, to clean the display panel.

16 Claims, 11 Drawing Sheets

(51) Int. Cl.
*H01L 25/16* (2023.01)
*H01L 27/15* (2006.01)

(56) References Cited

U.S. PATENT DOCUMENTS

2011/0256019 A1   10/2011  Gruen et al.
2018/0147417 A1*  5/2018  Rantala .................. H01L 33/08

FOREIGN PATENT DOCUMENTS

| CN | 112599017 A | 4/2021 |
| CN | 113589586 A | 11/2021 |

OTHER PUBLICATIONS

Notification to Grant Patent Right for Invention dated Jun. 19, 2023 issued in CN 202310287264.9.

* cited by examiner

DISPLAY DEVICE AND ELECTRONIC DEVICE

CROSS-REFERENCE TO RELATED APPLICATIONS

This application claims priority under 35 U.S.C. § 119(a) to Chinese Patent Application No. 202310287264.9, filed Mar. 23, 2023, the entire disclosure of which is incorporated herein by reference.

TECHNICAL FIELD

This disclosure relates to the field of display technology, and in particular to a display device and an electronic device.

BACKGROUND

With the development of artificial intelligence technology, touch interaction screens in the office, scientific research, medical, automotive, aerospace, and other fields are becoming more and more popular, for example, touch screen displays are widely used in automatic ticket machines of the train and subway, machine control machines, medical, automotive, and many other directions.

But a disadvantage is that users of the touch interaction screen are complex, making a surface of a touch interaction screen tend to get dirty, especially public electronics can cause a large quantity of viruses and bacteria on the display screen, and many viruses and bacteria can stay on plastic and glass for two hours to a week. This has a very negative impact on human body, especially for the elderly, children, and other people with poor resistance, which means that touch interaction screens in public places need to be constantly disinfected to prevent spread of viruses

SUMMARY

In a first aspect, a display device is provided in the present disclosure. The display device includes a back plate, a display panel, an optical film, a first light-emitting unit, and a second light-emitting unit. The back plate includes a body portion and a carrier portion. The carrier portion is connected to a periphery of the body portion in a bent manner. The carrier portion includes a first sub-carrier portion and a second sub-carrier portion. The second sub-carrier portion is closer to an outer periphery of the back plate than the first sub-carrier portion. The second sub-carrier portion is farther away from the body portion than the first sub-carrier portion. The display panel is carried on the back plate. The display panel and the back plate cooperatively define an accommodating cavity. The display panel includes a display screen and a transparent cover plate. The display screen is carried on the second sub-carrier portion. The transparent cover plate is carried on the second sub-carrier portion. The transparent cover plate is farther away from the body portion than the display screen. The optical film is accommodated in the accommodating cavity. The first light-emitting unit is accommodated in the accommodating cavity and located on one side of the optical film away from the display panel. The first light-emitting unit is configured to emit visible light. The visible light emitted by the first light-emitting unit is incident on the display panel via the optical film. The second light-emitting unit is carried on the second sub-carrier portion of the back plate. The second light-emitting unit is configured to emit ultraviolet light. A part of the ultraviolet light emitted by the second light-emitting unit avoids the display screen and is emitted onto the transparent cover plate, and another part of the ultraviolet light emitted by the second light-emitting unit is emitted onto the transparent cover plate via the display screen, to clean the display panel.

In a second aspect, an electronic device is further disposed in the present disclosure. The electronic device includes a housing and a display device. The display device includes a back plate, a display panel, an optical film, a first light-emitting unit, and a second light-emitting unit. The back plate includes a body portion and a carrier portion. The carrier portion is connected to a periphery of the body portion in a bent manner. The carrier portion includes a first sub-carrier portion and a second sub-carrier portion. The second sub-carrier portion is closer to an outer periphery of the back plate than the first sub-carrier portion. The second sub-carrier portion is farther away from the body portion than the first sub-carrier portion. The display panel is carried on the back plate. The display panel and the back plate cooperatively define an accommodating cavity. The display panel includes a display screen and a transparent cover plate. The display screen is carried on the second sub-carrier portion. The transparent cover plate is carried on the second sub-carrier portion. The transparent cover plate is farther away from the body portion than the display screen. The optical film is accommodated in the accommodating cavity. The first light-emitting unit is accommodated in the accommodating cavity and located on one side of the optical film away from the display panel. The first light-emitting unit is configured to emit visible light. The visible light emitted by the first light-emitting unit is incident on the display panel via the optical film. The second light-emitting unit is carried on the second sub-carrier portion of the back plate. The second light-emitting unit is configured to emit ultraviolet light. A part of the ultraviolet light emitted by the second light-emitting unit avoids the display screen and is emitted onto the transparent cover plate, and another part of the ultraviolet light emitted by the second light-emitting unit is emitted onto the transparent cover plate via the display screen, to clean the display panel. The housing is configured to accommodate the display device.

BRIEF DESCRIPTION OF THE DRAWINGS

To describe the technical solutions in implementations of the present disclosure or in the related art more clearly, the following briefly describes the accompanying drawings required for describing the implementations or the related art. Apparently, the accompanying drawings in the following description show merely some implementations of the present disclosure, and a person of ordinary skill in the art may still derive other drawings from these accompanying drawings without creative efforts.

REFERENCE SIGNALS

1—electronic device, 10—display device, 20—housing, 11—back plate, 12—display panel, 13—optical film, 14—first light-emitting unit, 15—second light-emitting unit, 16—accommodating cavity, 17—prism sheet, 18—cover plate, 111—body portion, 112—carrier portion, 113—accommodating groove, 121—display screen, 122—transparent cover plate, 171—first prism sub-sheet, 172—second prism sub-sheet, 1121—first sub-carrier portion, 1122—second sub-carrier portion, 1131—light-transmitting opening, 1132—first accommodating sub-groove, 1133—second accommodating sub-groove, 1134—receiving opening, 1711—first base, 1712—first prism column, 1721—second base, 1722—second prism column, 112a—first carrier surface, 112b—connecting surface, 112c—second carrier surface, 113a—first portion, 113b—second portion, 113c—third portion, 113d—first opening, 113e—second opening.

DETAILED DESCRIPTION

Technical solutions of implementations of the present disclosure will be described clearly and completely with reference to accompanying drawings in implementations of the present disclosure. Apparently, implementations described herein are merely some implementations, rather than all implementations, of the present disclosure. Based on implementations of the present disclosure, all other implementations obtained by those of ordinary skill in the art without creative effort shall fall within the protection scope of the present disclosure.

Terms "first", "second", and the like used in the specification, the claims, and the accompany drawings of the present disclosure are used to distinguish different objects rather than describe a particular order. In addition, the terms "include", "comprise", and "have" as well as variations thereof are intended to cover non-exclusive inclusion. For example, a process, a method, a system, a product, or a device including a series of operations or units is not limited to the listed operations or units, it can optionally include other operations or units that are not listed; alternatively, other operations or units inherent to the process, the method, the product, or the device can be included either.

A term "implementation" referred to herein means that a particular feature, structure, or characteristic described in conjunction with implementations may be contained in at least one implementation of the present disclosure. The phrase appearing in various places in the specification does not necessarily refer to the same implementation, nor does it refer an independent or alternative implementation that is mutually exclusive with other implementations. It is expressly and implicitly understood by those skilled in the art that an implementation described herein may be combined with other implementations.

Figure 1:
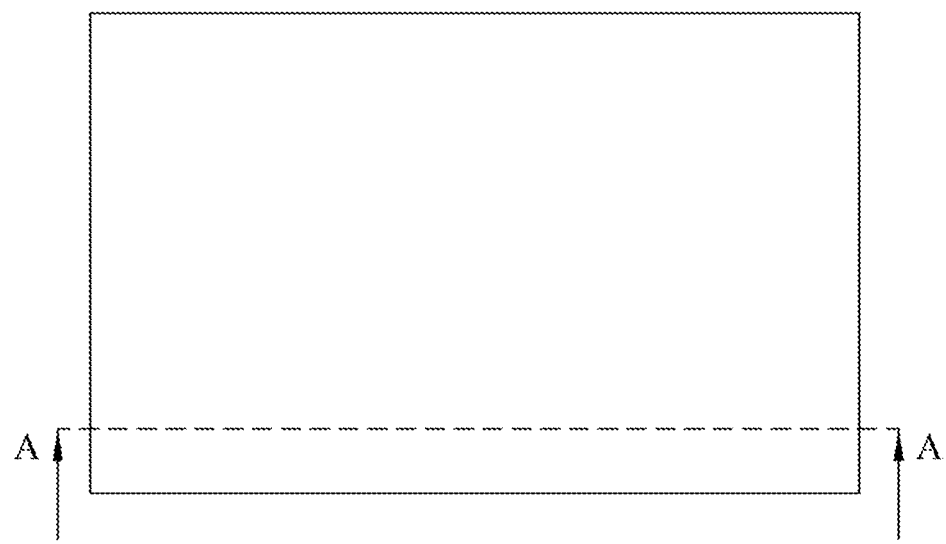
FIG. 1 is a schematic diagram of a display device in an implementation of the present disclosure.
Figure 2:
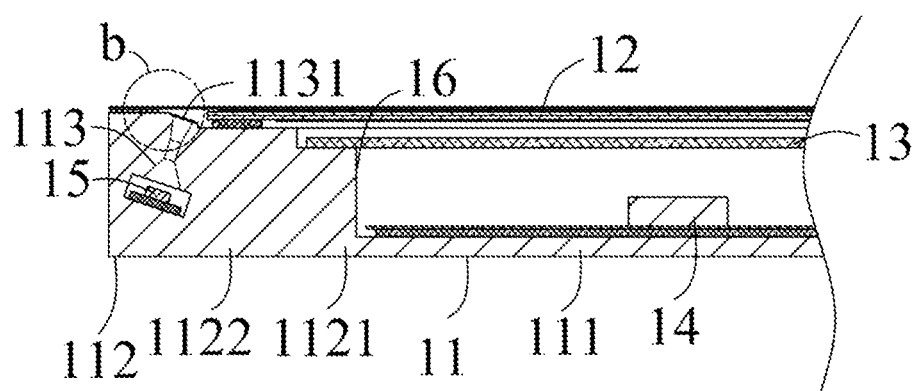
FIG. 2 is a partial schematic cross-sectional structural diagram of the display device in FIG. 1 along line A-A.
Figure 3:
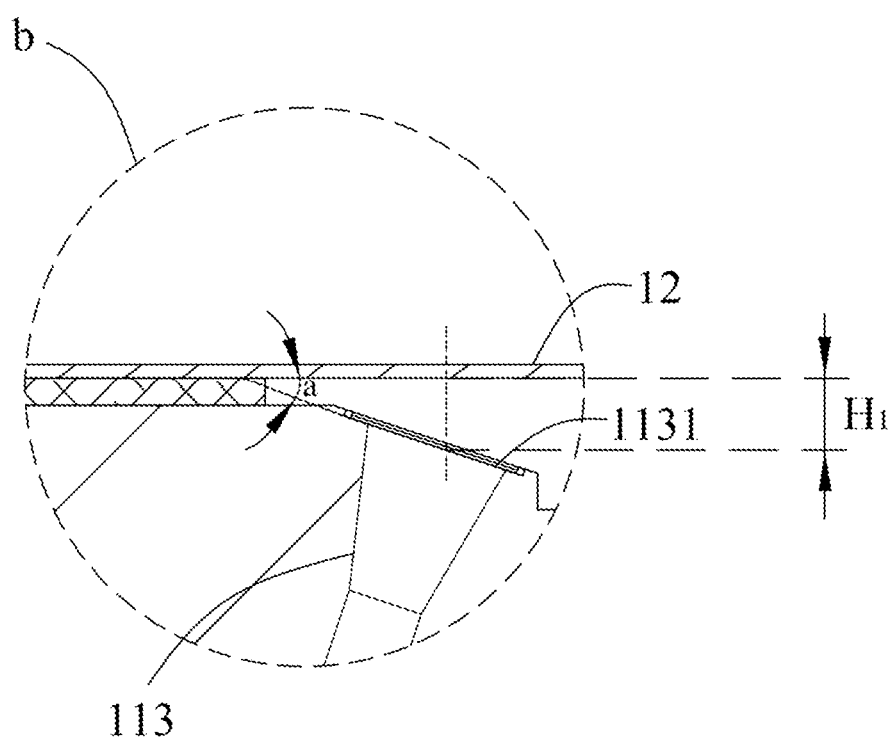
FIG. 3 is a schematic partial enlarged view of a cross sectional structure of the display device in FIG. 2.
Figure 4:
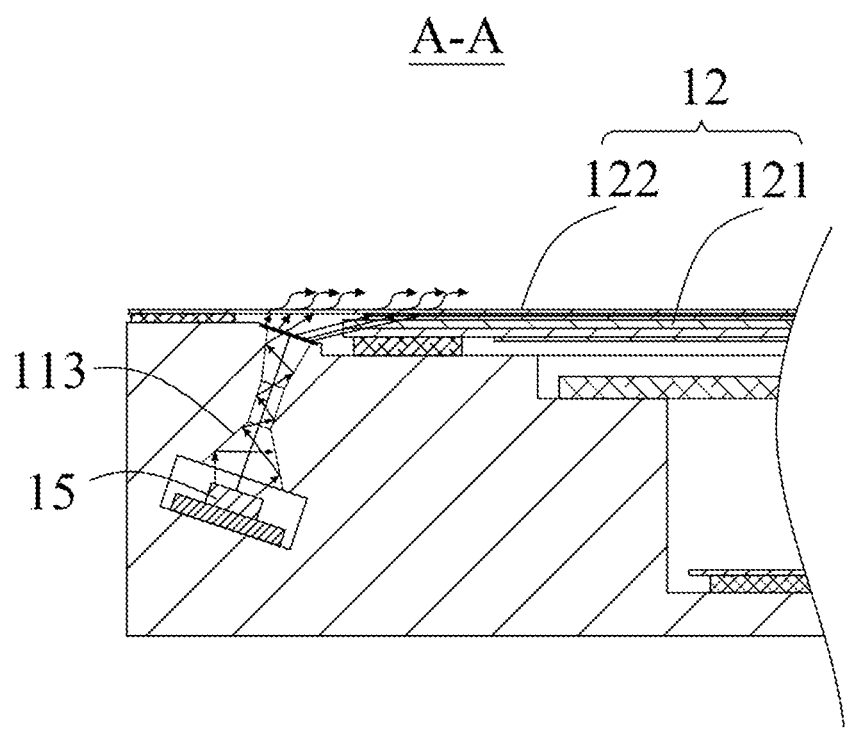
FIG. 4 is a schematic diagram of optical paths of a display device in an implementation of the present disclosure.
Figure 8:
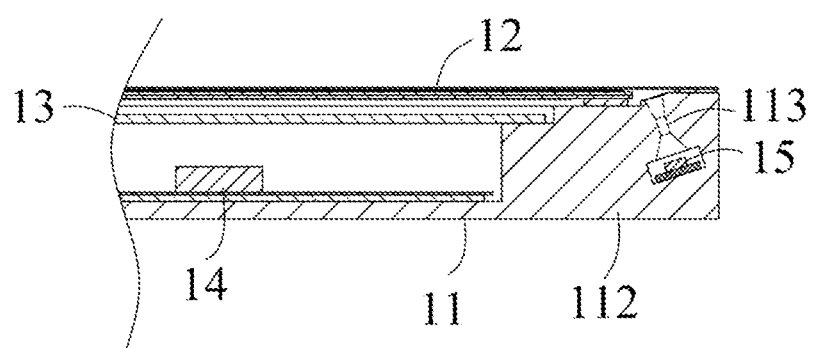
FIG. 8 is a partial schematic cross-sectional structural diagram of a display device along line A-A in yet another implementation of the present disclosure.

Refer to FIG. 1, FIG. 2, FIG. 3, FIG. 4, and FIG. 8. FIG. 1 is a schematic diagram of a display device in an implementation of the present disclosure, FIG. 2 is a partial schematic cross-sectional structural diagram of the display device in FIG. 1 along line A-A, FIG. 3 is a schematic partial enlarged view of a cross sectional structure of the display device in FIG. 2, FIG. 4 is a schematic diagram of optical paths of a display device in an implementation of the present disclosure, and FIG. 8 is a partial schematic cross-sectional structural diagram of a display device along line A-A in yet another implementation of the present disclosure. A display device 10 is provided in the present disclosure. The display device 10 includes a back plate 11, a display panel 12, an optical film 13, a first light-emitting unit 14, and a second light-emitting unit 15. The display panel 12 is carried on the back plate 11, and the display panel 12 and the back plate 11 cooperatively define an accommodating cavity 16. The optical film 13 is accommodated in the accommodating cavity 16. The first light-emitting unit 14 is accommodated in the accommodating cavity 16 and located on one side of the optical film 13 away from the display panel 12. The first light-emitting unit 14 is configured to emit visible light, and the visible light emitted by the first light-emitting unit 14 is incident on the display panel 12 via the optical film 13. The second light-emitting unit 15 is carried on the back plate 11. The second light-emitting unit 15 is configured to emit ultraviolet light. The ultraviolet light emitted by the second light-emitting unit 15 at least partially avoids the optical film 13 and is emitted to the display panel 12, to clean the display panel 12.

The display device 10 may be, but is not limited to, a Thin Film Transistor Liquid Crystal Display (TFT-LCD), or a Mini Light Emitting Diode (Mini LED) display, or a Mini Light Emitting Diode (Micro LED) display, or the like. It can be understood that the display device 10 may be a display with another architecture. The display device 10 may be, but is not limited to, a touch interaction display device 10. It can be understood that the display device 10 may alternatively be a display device 10 of another functional type, and a functional type of the display device 10 does not constitute a limitation on the display device 10 provided in this implementation. The display device 10 may include, but is not limited to, the back plate 11, the display panel 12, the optical film 13, the first light-emitting unit 14, the second light-emitting unit 15, and the like. The display device 10 may also include other components, such as a middle frame and a reflecting plate. It can be understood that other components of the display device 10 does not constitute a limitation on the display device 10 provided in this implementation.

A material of the back plate 11 may be, but is not limited to, plastic, metal, composite material, or the like. It can be understood that the back plate 11 may alternatively be made of another material. The material of the back plate 11 does not constitute a limitation on the display device 10 provided in this implementation. The back plate 11 may be, but is not limited to, configured to carry the display panel 12, the optical film 13, the first light-emitting unit 14, and the second light-emitting unit 15.

The display panel 12 is carried on the back plate 11. The display panel 12 and the back plate 11 may be, but are not limited to, fixed by using a foam tape. The display panel 12 may include, but is not limited to, a thin film transistor (TFT) substrate, a color filter substrate, a liquid crystal layer, a transparent cover plate 122, and the like. The display panel 12 is configured to display a picture in the display device 10.

The optical film 13 is accommodated in the accommodating cavity 16. The optical film 13 may be, but is not limited to, carried on the back plate 11. The optical film 13 and the back plate 11 may be, but are not limited to, fixed by using a foam tape.

The first light-emitting unit 14 may be, but is not limited to a Light Emitting Diode (LED) lamp bead. The first light-emitting unit 14 is accommodated in the accommodating cavity 16 and located on the one side of the optical film 13 away from the display panel 12. The first light-emitting unit 14 may have, but is not limited to, a specific spacing distance from the optical film 13. The first light-emitting unit 14 is configured to emit visible light, and the visible light emitted by the first light-emitting unit 14 may be, but is not limited to, incident on the display panel 12 via the optical film 13, to provide a light source for the display panel 12. The first light-emitting unit 14 may adopt, but is not limited to, a side light-incident manner or a bottom light-incident manner. It can be understood that a manner in which the first light-emitting unit 14 provides the light source for the display panel 12 does not constitute a limitation on the display device 10 provided in the implementation.

The second light-emitting unit 15 may be, but is not limited to, an ultraviolet light lamp bead, and configured to emit ultraviolet light. Ultraviolet light is an electromagnetic wave with a wavelength from 270 mm to 285 mm, which is invisible light, and has an excellent disinfection effect. When the ultraviolet light emitted by the second light-emitting unit 15 is emitted to the display panel 12, the ultraviolet light can pass through the display panel 12 and is used for cleaning and disinfecting an outer surface of the display panel 12. Specifically, a principle of the ultraviolet light emitted by the second light-emitting unit 15 cleaning the display panel 12 is that an electromagnetic wave in this wave band can damage a molecular structure of Deoxyribonucleic Acid (DNA) or Ribonucleic Acid (RNA) in the cells of microorganisms, causing growth cell death and/or regenerative cell death, to disinfect the outer surface of the display panel 12.

The second light-emitting unit 15 may be, but is not limited to, carried on the back plate 11 in a manner of bonding, detachable connection, or the like. A quantity (that is, how many) of the second light-emitting units 15 may be, but is not limited to, one, two, three, or more. It can be understood that the quantity of the second light-emitting units 15 may be set according to an actual application situation of the display device 10 or through experimental data calculation. A set quantity of the second light-emitting units 15 does not constitute a limitation on the display device 10 provided in this implementation. The second light-emitting unit 15 may be, but is not limited to, arranged on two opposite sides of the display panel 12. A length size of the second light-emitting unit 15 may be, but is not limited to, 6.8 mm, a width size of the second light-emitting unit 15 may be, but is not limited to, 6.8 mm, and a height size of the second light-emitting unit 15 may be, but is not limited to, 2.1 mm. That is, a size specification of a length, a width, and a height of the second light-emitting unit 15 may be, but is not limited to, 6.8×6.8×2.1 mm, so that a space ratio of the second light-emitting unit 15 in the display device 10 is very small, which is conducive to lighting and thinning design of the display device 10. It can be understood that the second light-emitting unit 15 may be with another size specification, and the size specification of the second light-emitting unit 15 does not constitute a limitation on the display device 10 provided in this implementation.

The ultraviolet light emitted by the second light-emitting unit 15 may partially or all avoid the optical film 13 and exit to the display panel 12, but the present disclosure is not limited thereto. In an implementation, the ultraviolet light emitted by the second light-emitting unit 15 all or basically all avoids the optical film 13, so that the ultraviolet light emitted by the second light-emitting unit 15 is directly emitted to the display panel 12, to reduce waste of the ultraviolet light and clean the display panel 12 to a relatively strong extent. In an implementation of the present disclosure (FIG. 4), the ultraviolet light emitted by the second light-emitting unit 15 may be partially emitted onto the outer surface of the display panel 12 via the liquid crystal layer of the display panel 12, and partially avoid the liquid crystal layer of the display panel 12 and be emitted onto the outer surface of the display panel 12 via the transparent cover plate 122 of the display panel 12, thereby further improving clean strength of the display panel 12 to fully achieve disinfection, but the present disclosure is not limited thereto.

Based on the above, the display device 10 cleans the display panel 12 by using the ultraviolet light emitted by the second light-emitting unit 15, and may cancel disinfection of the display device 10 in a manner of manual spraying and wiping, to reduce costs of manpower and materials. In addition, the display device 10 disinfects in a manner of self-emitting ultraviolet light, which has low costs, simple operation, short disinfection time, and high efficiency. The ultraviolet light emitted by the second light-emitting unit 15 provided in this implementation at least partially avoids the optical film 13, and can be directly emitted via the transparent cover plate 122 of the display panel 12, to reduce waste and loss of the ultraviolet light, so that the display panel 12 receives the ultraviolet light to a greater extent and use efficiency of the ultraviolet light is improved, to fully clean and disinfect the display panel 12. The ultraviolet light emitted by the second light-emitting unit 15 can not only disinfect the surface of the display panel 12, but also clean air around the display device 10, to effectively protect health of a user of the display device 10.

Figure 5:
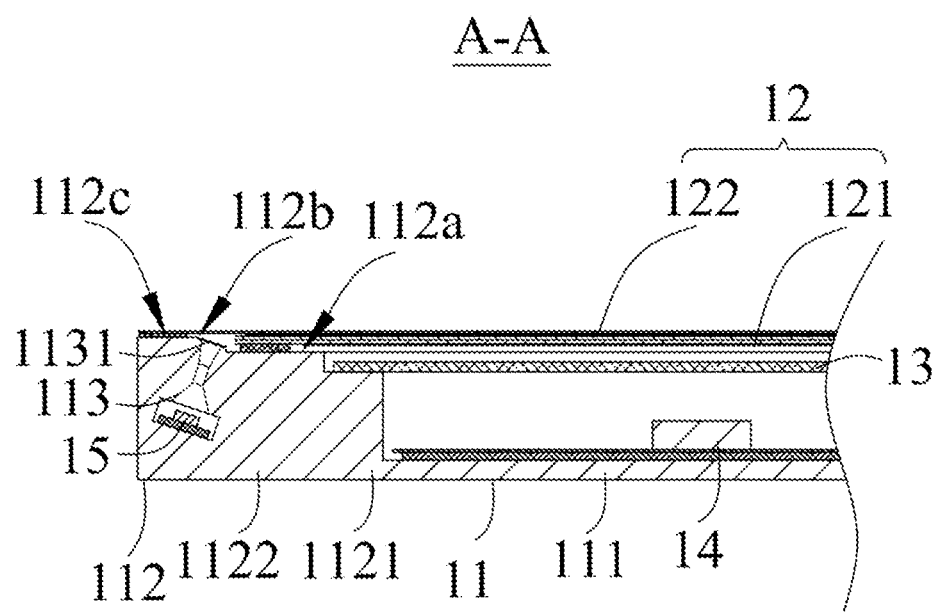
FIG. 5 is a partial schematic cross-sectional structural diagram of a display device along line A-A in an implementation of the present disclosure.
Figure 9:
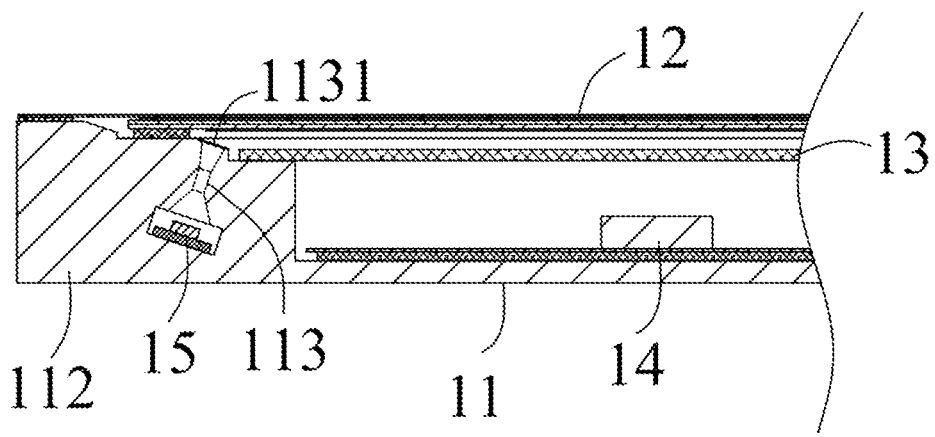
FIG. 9 is a partial schematic cross-sectional structural diagram of a display device along line A-A in yet another implementation of the present disclosure.

Refer to FIG. 5 and FIG. 9. FIG. 5 is a partial schematic cross-sectional structural diagram of a display device along line A-A in implementation 1 of the present disclosure, and FIG. 9 is a partial schematic cross-sectional structural diagram of a display device along line A-A in yet another implementation of the present disclosure. The back plate 11 includes a body portion 111 and a carrier portion 112. The carrier portion 112 is connected to a periphery of the body portion 111 in a bent manner. The carrier portion 112 includes a first sub-carrier portion 1121 and a second sub-carrier portion 1122. The first sub-carrier portion 1121 is configured to carry the optical film 13. The second sub-carrier portion 1122 is closer to an outer periphery of the back plate 11 than the first sub-carrier portion 1121. The second sub-carrier portion 1122 farther away from the body portion 111 than the first sub-carrier portion 1121. The second sub-carrier portion 1122 is configured to carry the display panel 12. The second sub-carrier portion 1122 defines an accommodating groove 113. The second light-emitting unit 15 is accommodated in the accommodating groove 113.

The body portion 111 may carry, but is not limited to, the first light-emitting unit 14. The carrier portion 112 is connected to a periphery of the body portion 111 in a bent manner. The carrier portion 112 and the body portion 111 may be, but are not limited to, integrally formed. A bent angle between the carrier portion 112 and the body portion 111 may be, but is not limited to, 90° or basically 90°. In this implementation, an example in which the bent angle between the carrier portion 112 and the body portion 111 is 90° is used for illustration.

The first sub-carrier portion 1121 may be, but is not limited to, configured to carry the optical film 13. The first sub-carrier portion 1121 may be, but is not limited to, connected to the body portion 111 in a bent manner. A bent angle between the first sub-carrier portion 1121 and the body portion 111 may be, but is not limited to, 90° or basically 90°. In this implementation, an example in which the bent angle between the first sub-carrier portion 1121 and the body portion 111 is 90° is used for illustration. The first sub-carrier portion 1121 may be, but is not limited to, integrally formed with the body portion 111.

The second sub-carrier portion 1122 may be, but is not limited to, configured to carry the display panel 12. The second sub-carrier portion 1122 may be, but is not limited to, integrally formed with the first sub-carrier portion 1121. The display panel 12 covers the optical film 13, and the display panel 12 farther away from the body portion 111 than the optical film 13. To implement corresponding carrying function, the second sub-carrier portion 1122 is closer to the outer periphery of the back plate 11 than the first sub-carrier portion 1121, and the second sub-carrier portion 1122 farther away from the body portion 111 than the first sub-carrier portion 1121.

The second sub-carrier portion 1122 defines an accommodating groove 113, and the second light-emitting unit 15 is accommodated in the accommodating groove 113. The accommodating groove 113 may be, but is not limited to, arranged at one end of the second sub-carrier portion 1122 close to the first sub-carrier portion 1121 (FIG. 9) or arranged on a part of the second sub-carrier portion 1122 close to the outer periphery of the back plate 11 (FIG. 2). When the accommodating groove 113 is defined at the one end of the second sub-carrier portion 1122 close to the first sub-carrier portion 1121, the ultraviolet light emitted by the second light-emitting unit 15 via the accommodating groove 113 may be, but is not limited to, emitted onto an inner surface of the display panel 12 and emitted onto the outer surface of the display panel 12 via the display panel 12. In an implementation, when the accommodating groove 113 is arranged on the part of the second sub-carrier portion 1122 close to the outer periphery of the back plate 11, the ultraviolet light emitted by the second light-emitting unit 15 via the accommodating groove 113 may be at least partially directly emitted to the transparent cover plate 122 of the display panel 12, and emitted to the outer surface of the display panel 12 via the transparent cover plate 122 of the display panel 12, to effectively reduce waste and loss of the ultraviolet light, so that the display panel 12 receives the ultraviolet light to a greater extent and use efficiency of the ultraviolet light is improved, to more fully clean and disinfect the display panel 12.

A quantity of the accommodating grooves 113 may be, but is not limited to, one, two, three, or more. The quantity of the accommodating grooves 113 may be, but is not limited to, equal to the quantity of the second light-emitting unit 15. The second light-emitting unit 15 is accommodated in the accommodating groove 113, and the accommodating groove 113 may be, but is not limited to, configured to converge the ultraviolet light emitted by the second light-emitting unit 15. Specifically, a side wall of the back plate 11 that forms the accommodating groove 113 may have, but is not limited to, a reflecting film layer. A material of the reflecting film layer may be, but is not limited to, gold, or other materials that can reflect ultraviolet light, such as, titanium dioxide or zinc oxide, so that the ultraviolet light emitted by the second light-emitting unit 15 can be reflected by the side wall of the back plate 11 that forms the accommodating groove 113 to an exit of the accommodating groove 113, to implement converging of the ultraviolet light emitted by the second light-emitting unit 15. In addition, when there is a spacing between the second light-emitting unit 15 and the display panel 12, more ultraviolet light is emitted onto the display panel 12, to avoid loss of the ultraviolet light, so that the display panel 12 receives and transmits a larger quantity of waves more fully while ensuring security.

Refer to FIG. 2 and FIG. 3. The accommodating groove 113 has a light-transmitting opening 1131 for ultraviolet light to pass through. A plane on which the light-transmitting opening 1131 is located and a plane on which the display panel 12 is located defines an angle a therebetween. The angle a satisfies: $15° \leq a \leq 30°$.

The light-transmitting opening 1131 may be, but is not limited to, in a shape of a circle, a square, a rectangle, or in another irregular shape. In an implementation, an example in which the light-transmitting opening 1131 is in a shape of a circle is used for illustration, so that the ultraviolet light has a uniformly emitting effect. There is the angle a between the plane on which the light-transmitting opening 1131 is located and the plane on which the display panel 12 is located, and the angle a may be, but is not limited to, 15°, 20°, 25°, 30°, or the like. It can be understood that the angle a may be another degree, provided that the angle a satisfies 15° C. a≤30°.

When the angle a is less than 15°, most of the ultraviolet light emitted by the second light-emitting unit 15 via the light-transmitting opening 1131 is emitted via a peripheral side of the display panel 12. A disinfection effect for a central part of the display panel 12 is relatively weak, and a security problem exists. When the angle a is greater than 30°, more parts of the ultraviolet light emitted by the second light-emitting unit 15 via the light-transmitting opening 1131 is emitted onto the liquid crystal layer of the display panel 12. A disinfection effect for the outer surface of the display panel 12 is relatively weak, so that ultraviolet light at a higher power is required for a better disinfection and cleaning effect. Therefore, in an implementation, the angle a satisfies 15°≤a≤30°, to fully disinfect the display panel 12, and has a relatively greater cleaning strength and ensures security, so that the ultraviolet light emitted by the second light-emitting unit 15 is emitted in a side-and-inclined direction of the display device 10 and is prevented from being emitted to a person and affecting health of the person. In addition, the ultraviolet light emitted by the second light-emitting unit 15 covers a larger area on the display panel 12, effectively improving cleaning efficiency of the ultraviolet light emitted by the second light-emitting unit 15 for the display panel 12.

Refer to FIG. 4. The display panel 12 includes a display screen 121 and the transparent cover plate 122. The display screen 121 is carried on the second sub-carrier portion 1122. The transparent cover plate 122 is carried on the second sub-carrier portion 1122, and the transparent cover plate 122 farther away from the body portion 111 than the display screen 121. A part of the ultraviolet light emitted by the second light-emitting unit 15 avoids the display screen 121 and is emitted onto the transparent cover plate 122, and another part of the ultraviolet light emitted by the second light-emitting unit 15 is emitted onto the transparent cover plate 122 via the display screen 121.

The display screen 121 may include, but is not limited to, a Thin Film Transistor (TFT) substrate, a color filter substrate, and a liquid crystal layer. The display screen 121 is carried on the second sub-carrier portion 1122, and the display screen 121 and the second sub-carrier portion 1122 may be, but is not limited to, fixed by using a foam tape, to reduce shakes of the display screen 121, so that the display screen 121 stably displays a picture.

The transparent cover plate 122 may be, but is not limited to, configured to protect the display screen 121 from external pollution and damage. A material of the transparent cover plate 122 may be, but is not limited to, glass, plastic, other composite materials, or the like. The transparent cover plate 122 is carried on the second sub-carrier portion 1122, and the transparent cover plate 122 may be, but is not limited to, fixed to the second sub-carrier portion 1122 by using a foam tape. The transparent cover plate 122 farther away from the body portion 111 than the display screen 121. The transparent cover plate 122 may cover, but is not limited to, the display screen 121, to protect the display screen 121.

In this implementation, a part of the ultraviolet light emitted by the second light-emitting unit 15 avoids the display screen 121 and is emitted onto the transparent cover plate 122, and another part of the ultraviolet light emitted by the second light-emitting unit 15 is emitted onto the transparent cover plate 122 via the display screen 121, to effectively reduce waste and loss of the ultraviolet light, so that the display panel 12 receives the ultraviolet light to a greater extent and use efficiency of the ultraviolet light is improved, to more fully clean and disinfect the display panel 12.

Refer to FIG. 5. The second sub-carrier portion 1122 has a first carrier surface 112a, a connecting surface 112b, and a second carrier surface 112c. The first carrier surface 112a is configured to carry the display screen 121. The connecting surface 112b is connected to the first carrier surface 112a in a bent manner. The connecting surface 112b is inclined relative to the first carrier surface 112a. The connecting surface 112b defines the light-transmitting opening 1131. An orthographic projection of the transparent cover plate 122 on the back plate 11 covers the light-transmitting opening 1131. The second carrier surface 112c is connected to the connecting surface 112b in a bent manner. The second carrier surface 112c is closer to the outer periphery of the back plate 11 than the first carrier surface 112a. The second carrier surface 112c is farther away from the body portion 111 than the first carrier surface 112a. The second carrier surface 112c is configured to carry the transparent cover plate 122.

The first carrier surface 112a may be, but is not limited to, configured to carry the display screen 121. The display screen 121 may be, but is not limited to, fixedly connected to the first carrier surface 112a by using a foam tape. The first carrier surface 112a may be, but is not limited to, a plane or basically a plane. The first carrier surface 112a may be, but is not limited to, parallel to or basically parallel to the display screen 121.

The connecting surface 112b is connected to the first carrier surface 112a in a bent manner, and the connecting surface 112b may be, but is not limited to, inclined relative to the first carrier surface 112a. An inclination angle of the connecting surface 112b relative to the first carrier surface 112a may be, but is not limited to, 15°, 20°, 25°, or 30°. It can be understood that, the inclination angle between the connecting surface 112b and the first carrier surface 112a may alternatively be other degrees, and the inclination angle of the connecting surface 112b relative to the first carrier surface 112a does not constitute a limitation on the display device 10 provided in this implementation.

The second carrier surface 112c may be, but is not limited to, configured to carry the transparent cover plate 122, and the transparent cover plate 122 may be, but is not limited to, fixedly connected to the second carrier surface 112c by using a foam tape. The second carrier surface 112c may be, but is not limited to, a plane or basically a plane. The second carrier surface 112c may be, but is not limited to, parallel to or basically parallel to the transparent cover plate 122. The second carrier surface 112c is closer to the outer periphery of the back plate 11 than the first carrier surface 112a, and the second carrier surface 112c farther away from the body portion 111 than the first carrier surface 112a. Specifically, an orthogonal projection of the transparent cover plate 122 on the back plate 11 may be, but is not limited to, greater than an orthogonal projection of the display screen 121 on the back plate 11. The transparent cover plate 122 is farther away from the body portion 111 than the display screen 121, to cover and protect the display screen 121. Correspondingly, the second carrier surface 112c is closer to the outer periphery of the back plate 11 than the first carrier surface 112a, and the second carrier surface 112c farther away from the body portion 111 than the first carrier surface 112a, to support the transparent cover plate 122.

The connecting surface 112b may define, but is not limited to, the light-transmitting opening 1131, and the orthogonal projection of the transparent cover plate 122 on the back plate 11 may cover, but is not limited to, the light-transmitting opening 1131, so that the ultraviolet light emitted by the second light-emitting unit 15 via the light-transmitting opening 1131 may be directly emitted onto the transparent cover plate 122. In addition, the connecting surface 112b is arranged between the plane on which the transparent cover plate 122 is located and the plane on which the display screen 121 is located, so that the ultraviolet light emitted via the light-transmitting opening 1131 effectively avoids the optical film 13, is partially directly emitted to the transparent cover plate 122, and is partially emitted to the transparent cover plate 122 via the display screen 121. Therefore, the ultraviolet light emitted by the second light-emitting unit 15 can fully disinfect the display panel 12 while effectively covering the display panel 12, to effectively protect security and health of a user.

Figure 6:
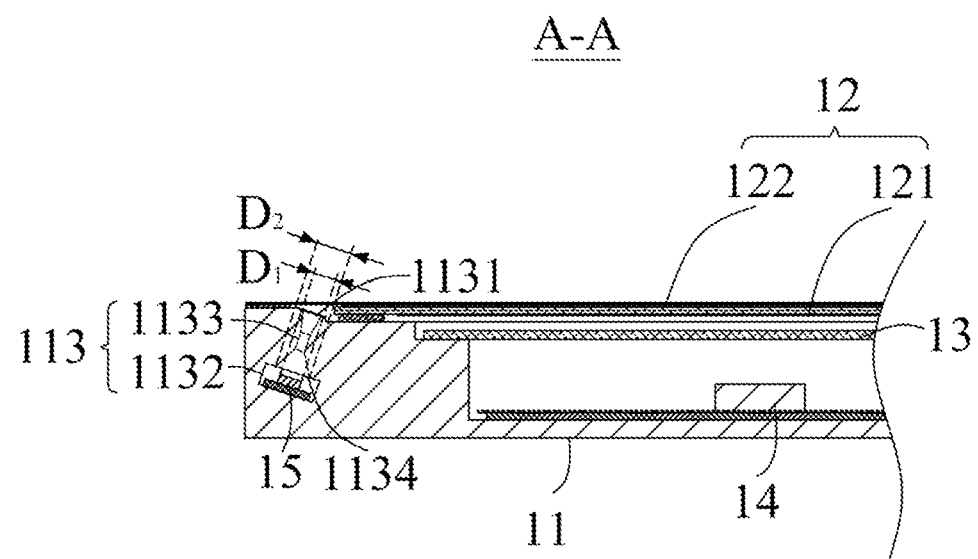
FIG. 6 is a partial schematic cross-sectional structural diagram of a display device along line A-A in another implementation of the present disclosure.
Figure 18:
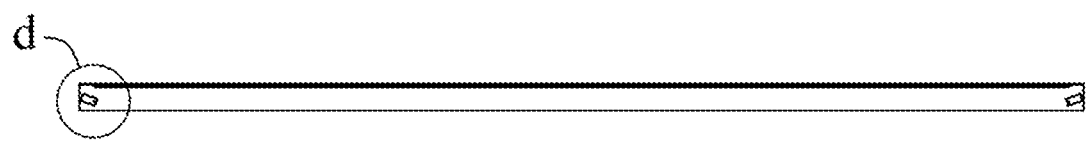
FIG. 18 is a schematic structural side view of a display device in an implementation of the present disclosure.
Figure 19:
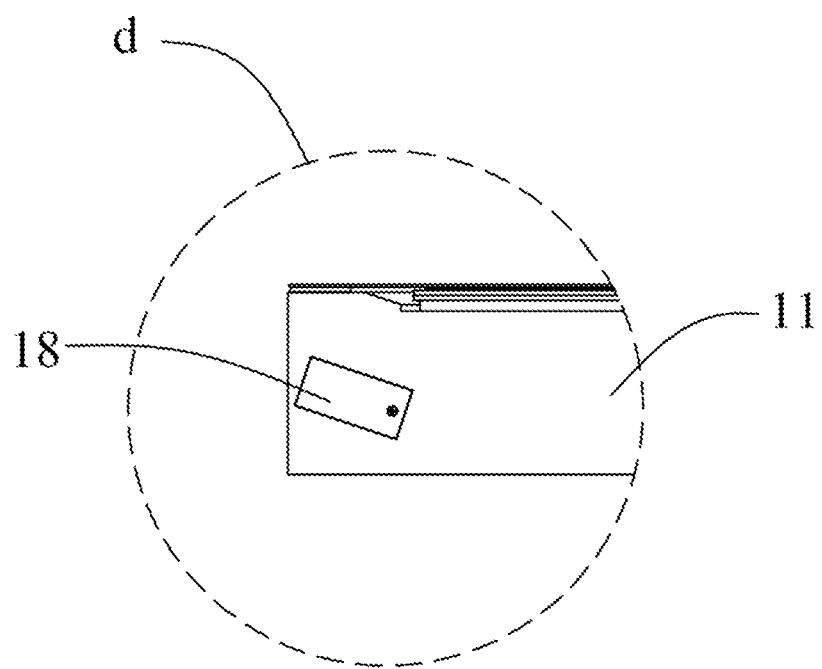
FIG. 19 is a partial enlarged schematic structural diagram of the display device in FIG. 18.
Figure 20:
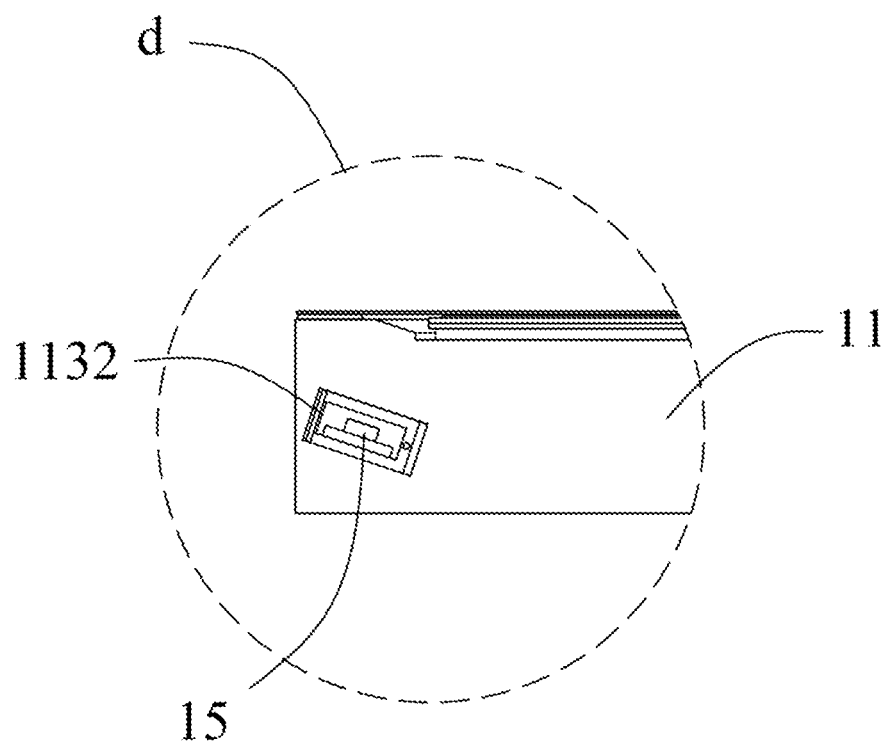
FIG. 20 is a partial enlarged schematic structural diagram of a display device in yet another implementation of the present disclosure.

Refer to FIG. 6, FIG. 18, FIG. 19, and FIG. 20. FIG. 6 is a partial schematic cross-sectional structural diagram of a display device along line A-A in another implementation of the present disclosure, FIG. 18 is a schematic structural side view of a display device in an implementation of the present disclosure, FIG. 19 is a partial enlarged schematic structural diagram of the display device in FIG. 18, and FIG. 20 is a partial enlarged schematic structural diagram of a display device in yet another implementation of the present disclosure. The accommodating groove 113 includes a first accommodating sub-groove 1132 and a second accommodating sub-groove 1133. The second light-emitting unit 15 is accommodated in the first accommodating sub-groove 1132. The second accommodating sub-groove 1133 has a receiving opening 1134 and a light-transmitting opening 1131 opposite to the receiving opening 1134. The receiving opening 1134 of the second accommodating sub-groove 1133 communicates with the first accommodating sub-groove 1132. The light-transmitting opening 1131 of the second accommodating sub-groove 1133 is exposed beyond the second sub-carrier portion 1122. The second light-emitting unit 15 has a size $D_1$ in a transverse direction. The receiving opening 1134 has a size $D_2$ in the transverse direction. The size $D_1$ and the size $D_2$ satisfies: $D_1 \leq D_2$.

The second light-emitting unit 15 is accommodated in the first accommodating sub-groove 1132. A shape of the first accommodating sub-groove 1132 may be, but is not limited to, a rectangle or a design of an approximate rectangle. A quantity of the first accommodating sub-grooves 1132 may be, but is not limited to, one, two, three, or more. The first accommodating sub-groove 1132 may communicate, but is not limited to, with the back plate 11, to facilitate mounting of the second light-emitting unit 15.

The display device 10 may further include, but is not limited to, a cover plate 18. The first accommodating sub-groove 1132 may have, but is not limited to, a port exposed on the back plate 11. The cover plate 18 is configured to cover the port of the first accommodating sub-groove 1132 exposed on the back plate 11. The cover plate 18 may be, but is not limited to, connected to the back plate 11 by a screw, a screw and a nut, or in other manners. In this implementation, an example in which the cover plate 18 is connected to the back plate 11 by a screw is used for illustration, so that a fixing effect is good. The cover plate 18 may be, but is not limited to, detachably connected to the back plate 11, to facilitate mounting of the second light-emitting unit 15. In addition, the second light-emitting unit 15 may be formed into a light bar, the light bar is inserted into the first accommodating sub-groove 1132 through the cover plate 18 that is detachably connected, and an operation is simple.

The second accommodating sub-groove 1133 has the receiving opening 1134 and the light-transmitting opening 1131 opposite to the receiving opening 1134. The receiving opening 1134 of the second accommodating sub-groove 1133 communicates with the first accommodating sub-groove 1132, so that the ultraviolet light emitted by the second light-emitting unit 15 is incident into the second accommodating sub-groove 1133 via the receiving opening 1134 of the second accommodating sub-groove 1133. The receiving opening 1134 may be, but is not limited to, in a shape of a circle, a square, or a rectangle, or in another irregular shape. In this implementation, an example in which the receiving opening 1134 is in a shape of a circle is used for illustration, so that the ultraviolet light can be uniformly emitted from the receiving opening 1134 into the second accommodating sub-groove 1133. The light-transmitting opening 1131 of the second accommodating sub-groove 1133 is exposed and arranged on the second sub-carrier portion 1122. The ultraviolet light emitted by the second light-emitting unit 15 is incident into the second accommodating sub-groove 1133 via the receiving opening 1134, and emitted to the display panel 12 via the light-transmitting opening 1131 of the second accommodating sub-groove 1133.

A side wall of the back plate 11 forming the second accommodating sub-groove 1133 may be, but is not limited to, coated with a reflecting film layer, and the side wall of the back plate 11 forming the second accommodating sub-groove 1133 may include, but is not limited to, the reflecting film layer. A material of the reflecting film layer may be, but is not limited to, gold or other materials that can reflect ultraviolet light, such as titanium dioxide or zinc oxide. The reflecting film layer can be configured to reflect the ultraviolet light emitted by the second light-emitting unit 15.

A plane on which the receiving opening 1134 is located may be, but is not limited to, parallel to a light emitting surface of the second light-emitting unit 15. The second light-emitting unit 15 has the size $D_1$ in the transverse direction, where the transverse direction may be, but is not limited to, a direction in which a diameter of the light emitting surface of the second light-emitting unit 15 is located. The receiving opening 1134 has the size $D_2$ in the transverse direction, where the transverse direction may be, but is not limited to, an extending direction of the plane on which the receiving opening 1134 is located. The size $D_1$ and the size $D_2$ satisfies: $D_1 \leq D_2$, so that the ultraviolet light emitted by the second light-emitting unit 15 can be fully emitted into the receiving opening 1134, and emitted via the second accommodating sub-groove 1133, to improve use efficiency of the ultraviolet light emitted by the second light-emitting unit 15.

Figure 7:
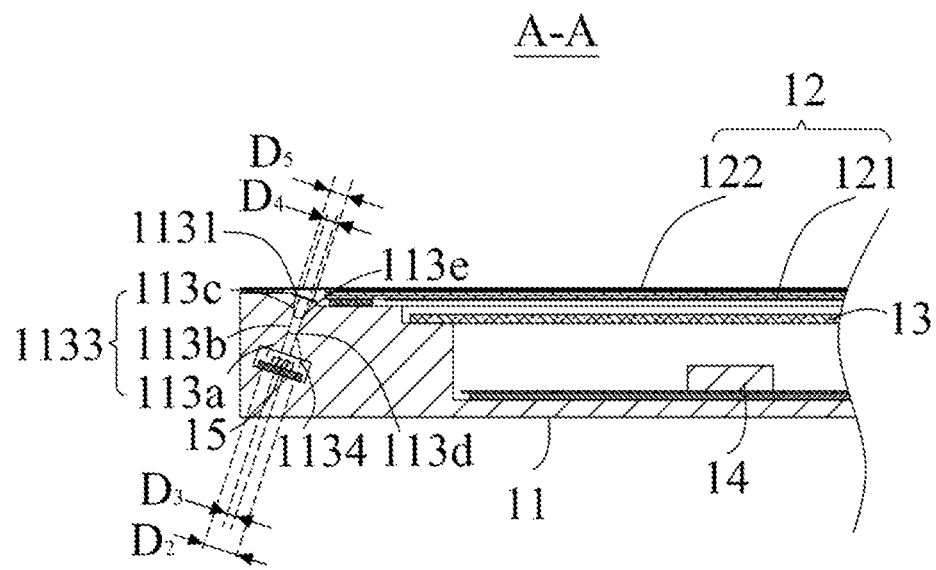
FIG. 7 is a partial schematic cross-sectional structural diagram of a display device along line A-A in yet another implementation of the present disclosure.

Refer to FIG. 7. FIG. 7 is a partial schematic cross-sectional structural diagram of a display device along line A-A in yet another implementation of the present disclosure. The second accommodating sub-groove 1133 includes a first portion 113a, a second portion 113b, and a third portion 113c. The first portion 113a is arranged close to the second light-emitting unit 15. One end of the first portion 113a close to the second light-emitting unit 15 defines the receiving opening 1134. The second portion 113b is arranged at one end of the first portion 113a away from the second accommodating sub-groove 1133. The second portion 113b communicates with the first portion 113a. The second portion 113b defines a first opening 113d and a second opening 113e opposite to the first opening 113d. The first opening 113d has a size $D_3$ in the transverse direction, and the second opening 113e has a size $D_4$ in the transverse direction. The third portion 113c is arranged at one end of the second portion 113b away from the first portion 113a, one end of the third portion 113c communicates with the second portion 113b, another end of the third portion 113c has the light-transmitting opening 1131, and the light-transmitting opening 1131 has a size $D_5$. The size $D_2$ of the receiving opening 1134 and the size $D_3$ of the first opening 113d satisfies: $D_2 \geq D_3$. The size $D_4$ of the second opening 113e and the size $D_5$ of the light-transmitting opening 1131 satisfies: $D_4 \leq D_5$.

The first portion 113a is arranged close to the second light-emitting unit 15, and one end of the first portion 113a close to the second light-emitting unit 15 has the receiving opening 1134 configured to receive the ultraviolet light emitted by the second light-emitting unit 15. A shape of the first portion 113a may be, but is not limited to, approximate horn-shaped, and a longitudinal section of the first portion 113a may be, but is not limited to, in a shape of a trapezoid or an approximate trapezoid.

The second portion 113b is arranged at one end of the first portion 113a away from the second accommodating sub-groove 1133. The second portion 113b communicates with the first portion 113a. The ultraviolet light emitted by the second light-emitting unit 15 is reflected by the first portion 113a to the second portion 113b. A shape of the second portion 113b may be, but is not limited to, a cylinder, and a longitudinal section of the second portion 113b may be, but is not limited to, in a shape of a rectangle or an approximate rectangle. The second portion 113b has the first opening 113d and the second opening 113e opposite to the first opening 113d. A shape of the first opening 113d may be, but is not limited to, a circle or an approximate circle. A shape of the second opening 113e may be, but is not limited to, a circle or an approximate circle. The first opening 113d has the size $D_3$ in the transverse direction, the second opening 113e has the size $D_4$ in the transverse direction, and a transverse size $D_3$ of the first opening 113d and a transverse size $D_4$ of the second opening 113e may be, but is not limited to, the same or basically the same.

A shape of the third portion 113c may be, but is not limited to, approximate horn-shaped, and a longitudinal section of the third portion 113c may be, but is not limited to, in a shape of a trapezoid or an approximate trapezoid. The third portion 113c is arranged at one end of the second portion 113b away from the first portion 113a, the one end of the third portion 113c communicates with the second portion 113b, and another end of the third portion 113c has the light-transmitting opening 1131. Light emitted by the second light-emitting unit 15 may be, but is not limited to, incident on the first portion 113a via the receiving opening 1134, then incident on the first opening 113d of the second portion 113b, reflected to the second opening 113e of the second portion 113b, then emitted to the third portion 113c, and reflected by the third portion 113c to the light-transmitting opening 1131 to be emitted.

The size $D_2$ of the receiving opening 1134 and the size $D_3$ of the first opening 113d satisfies: $D_2 \geq D_3$, and the size $D_4$ of the second opening 113e and the size $D_5$ of the light-transmitting opening 1131 satisfies: $D_4 \leq D_5$. That is, a shape design of the first portion 113a is similar to a horn, and a shape design of the third portion 113c is similar to a horn, so that a larger amount of the ultraviolet light emitted by the second light-emitting unit 15 can be more fully incident on the first portion 113a and the second portion 113b, and emitted via the third portion 113c. Therefore, more ultraviolet light can be emitted onto the display panel 12, to well clean the display panel 12.

Figure 10:
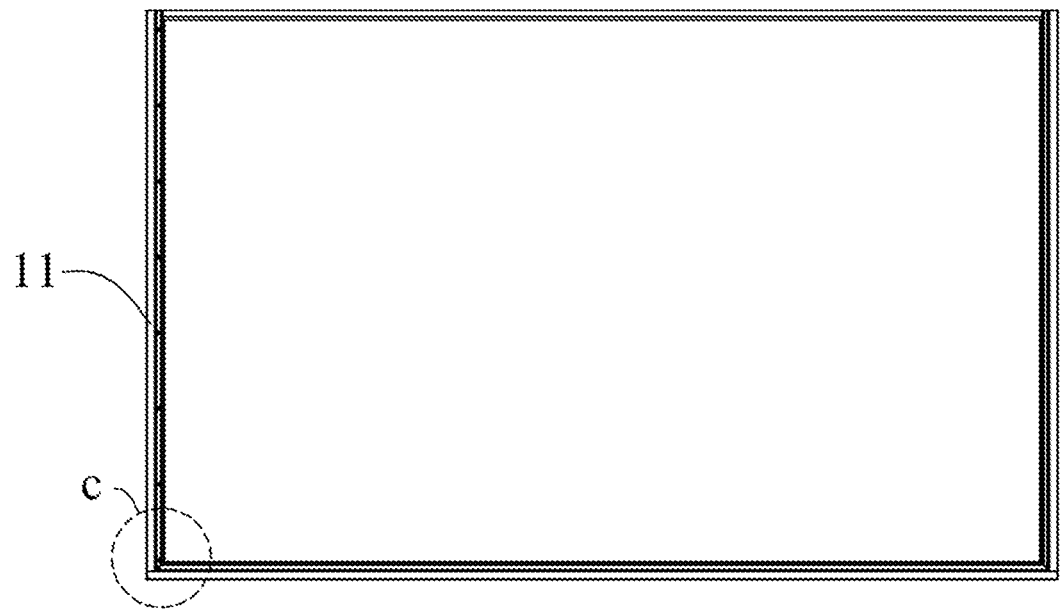
FIG. 10 is a partial schematic structural diagram of a display device in an implementation of the present disclosure.
Figure 11:
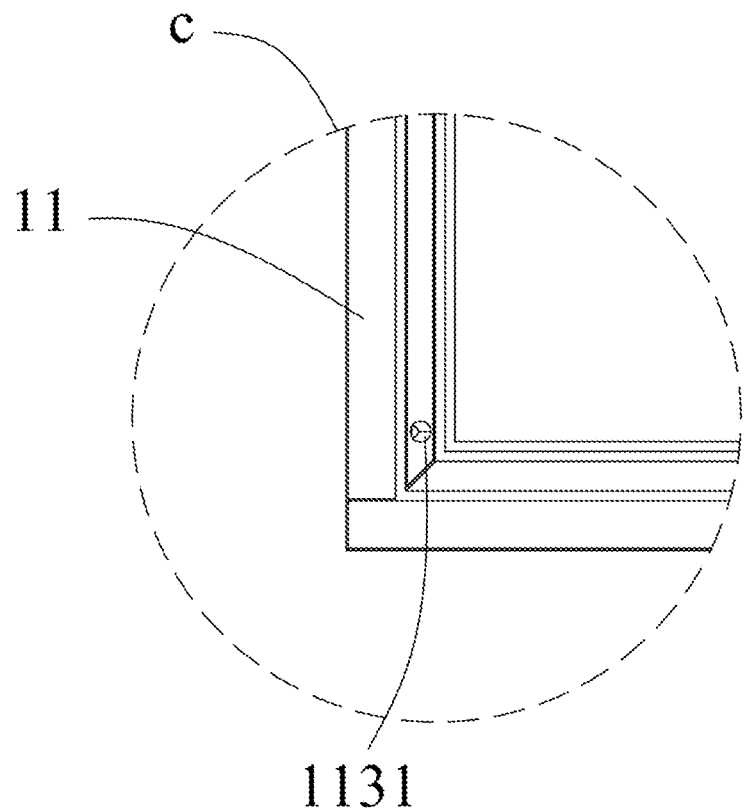
FIG. 11 is a partial enlarged schematic structural diagram of the display device in FIG. 10.
Figure 12:
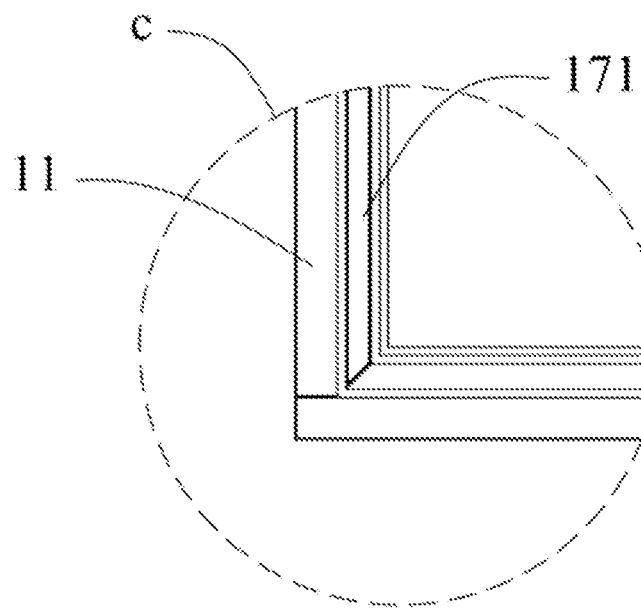
FIG. 12 is a partial enlarged schematic structural diagram of a display device in yet another implementation of the present disclosure.
Figure 13:
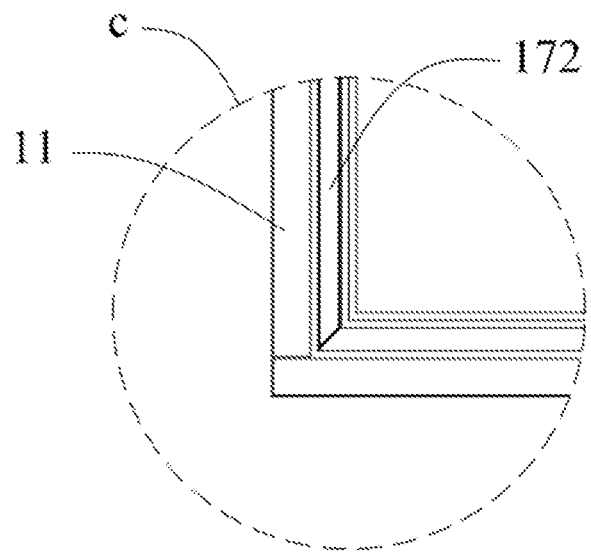
FIG. 13 is a partial enlarged schematic structural diagram of a display device in yet another implementation of the present disclosure.
Figure 14:
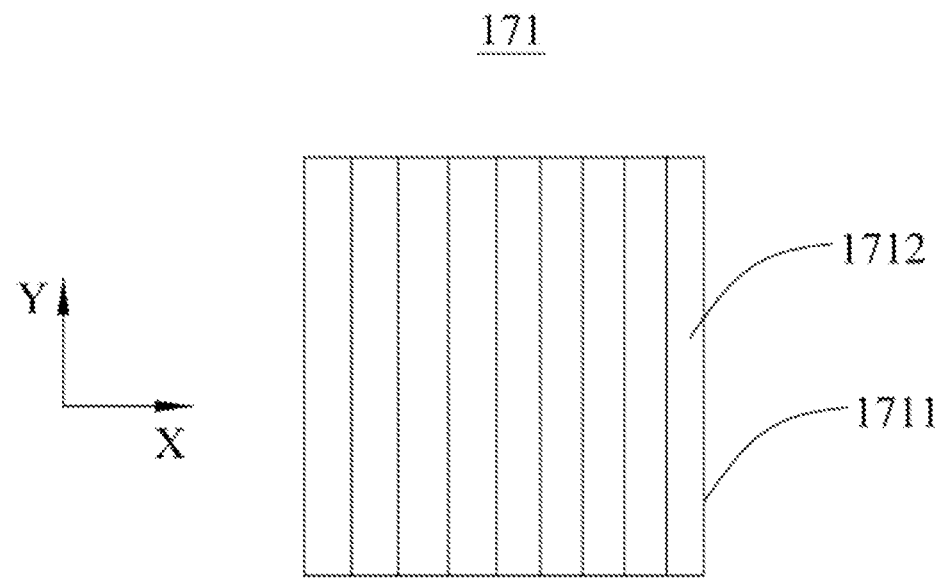
FIG. 14 is a schematic structural top view of a first prism sub-sheet in an implementation of the present disclosure.
Figure 15:
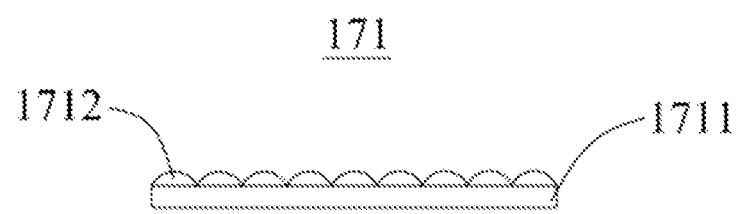
FIG. 15 is a schematic structural front view of a first prism sub-sheet in an implementation of the present disclosure.
Figure 16:
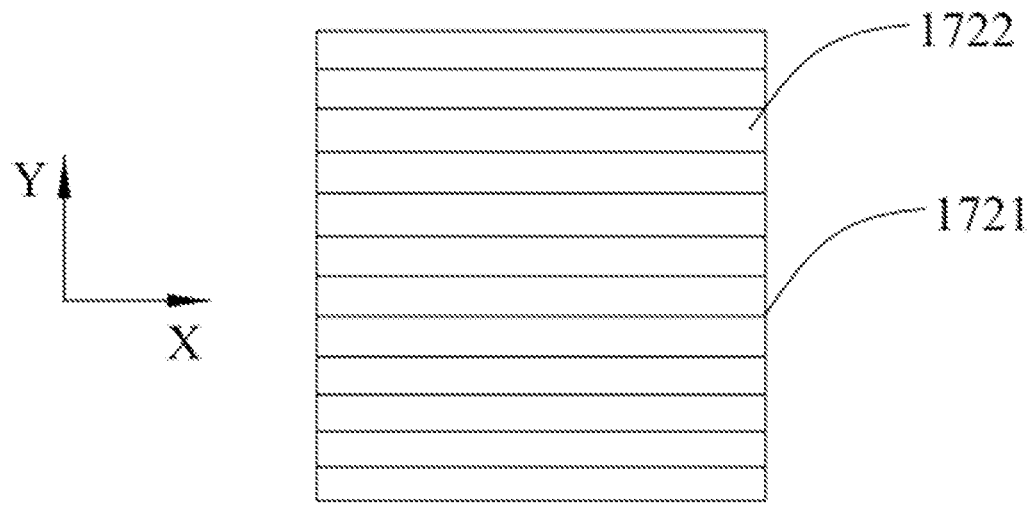
FIG. 16 is a schematic structural top view of a second prism sub-sheet in an implementation of the present disclosure.
Figure 17:
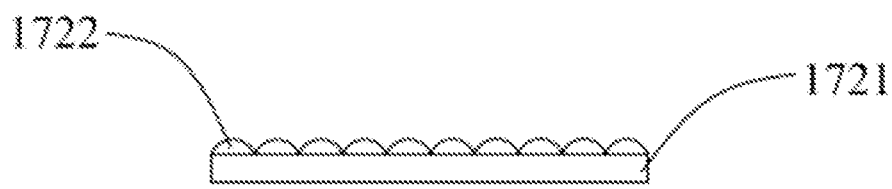
FIG. 17 is a schematic structural side view of a second prism sub-sheet in an implementation of the present disclosure.

Refer to FIG. 10, FIG. 11, FIG. 12, FIG. 13, FIG. 14, FIG. 15, FIG. 16, and FIG. 17. FIG. 10 is a partial schematic structural diagram of a display device in an implementation of the present disclosure, FIG. 11 is a partial enlarged schematic structural diagram of the display device in FIG. 10, FIG. 12 is a partial enlarged schematic structural diagram of a display device in yet another implementation of the present disclosure, FIG. 13 is a partial enlarged schematic structural diagram of a display device in yet another implementation of the present disclosure, FIG. 14 is a schematic structural top view of a first prism sub-sheet in an implementation of the present disclosure, FIG. 15 is a schematic structural front view of a first prism sub-sheet in an implementation of the present disclosure, FIG. 16 is a schematic structural top view of a second prism sub-sheet in an implementation of the present disclosure, and FIG. 17 is a schematic structural side view of a second prism sub-sheet in an implementation of the present disclosure. The display device 10 further includes a prism sheet 17. The prism sheet 17 is configured to cover the light-transmitting opening 1131. The prism sheet 17 includes a first prism sub-sheet 171 and a second prism sub-sheet 172. The first prism sub-sheet 171 and the second prism sub-sheet 172 are arranged in a stacked manner. The display device 10 has a first direction and a second direction. The first prism sub-sheet 171 includes a first base 1711 and a first prism column 1712. The first prism column 1712 is carried on the first base 1711 and the first prism column 1712 extends in the first direction. The second prism sub-sheet 172 includes a second base 1721 and a second prism column 1722. The second prism column 1722 is carried on the second base 1721 and the second prism column 1722 extends in the second direction. The first direction is orthogonal to the second direction.

The prism sheet 17 is configured to cover the light-transmitting opening 1131. The prism sheet 17 may be configured to adjust an emitting angle of the ultraviolet light. A shape of the prism sheet 17 may be, but is not limited to, a rectangle or basically a rectangle. The prism sheet 17 includes the first prism sub-sheet 171 and the second prism sub-sheet 172. The first prism sub-sheet 171 and the second prism sub-sheet 172 are arranged in a stacked manner. The first prism sub-sheet 171 may be, but is not limited to, bonded to or basically bonded to the second prism sub-sheet 172 for arrangement. A shape of the first prism sub-sheet 171 may be, but is not limited to, a rectangle or basically a rectangle. A shape of the second prism sub-sheet 172 may be, but is not limited to, a rectangle or basically a rectangle. A size of the second prism sub-sheet 172 may be, but is not limited to, the same as or basically the same as a size of the first prism sub-sheet 171.

The first prism sub-sheet 171 includes a first base 1711 and a first prism column 1712. The first prism column 1712 is carried on the first base 1711. The first prism column 1712 may be, but is not limited to, integrally formed with the first base 1711. A quantity of the first prism columns 1712 may be, but is not limited to, more than one. Multiple first prism columns 1712 may be, but is not limited to, uniformly arranged on the first base 1711. The first prism column 1712 is configured to refract light.

The second prism sub-sheet 172 includes the second base 1721 and the second prism column 1722. The second prism column 1722 is carried on the second base 1721. The second prism column 1722 may be, but is not limited to, integrally formed with the second base 1721. A quantity of the second prism columns 1722 may be, but is not limited to, more than one. Multiple second prism columns 1722 may be, but is not limited to, uniformly arranged on the second base 1721. The second prism column 1722 may be, but is not limited to, refract light.

The display device 10 has the first direction and the second direction. The first direction (as shown by Y in FIG. 14) may be, but is not limited to, perpendicular to a thickness direction of the first base 1711, and the first direction may be, but is not limited to, perpendicular to an arrangement direction of the multiple first prism columns 1712. The second direction (as shown by X in FIG. 16) may be, but is not limited to, perpendicular to a thickness direction of the second base 1721, and the second direction may be, but is not limited to, perpendicular to an arrangement direction of the multiple second prism columns 1722. The first direction may be, but is not limited to, orthogonal to or basically orthogonal to the second direction. The first prism column 1712 may extend, but is not limited to, in or basically in the first direction. The second prism column 1722 may extend, but is not limited to, in or basically in the second direction. The first direction is orthogonal to the second direction, that is, the first prism column 1712 is orthogonal or basically orthogonal to the second prism column 1722.

The first prism sub-sheet 171 may be, but is not limited to, a prism sheet with a specification of 0°, and the first prism sub-sheet 171 may be, but is not limited to, bonded the light-transmitting opening 1131 for arrangement. The second prism sub-sheet 172 may be, but is not limited to, a prism sheet with a specification of 90°, and the second prism sub-sheet 172 may be, but is not limited to, bonded to one side of the first prism sub-sheet 171 away from the light-transmitting opening 1131 for arrangement, so that an emitting angle of the ultraviolet light emitted from the light-transmitting opening 1131 may be controlled within 60° through refraction of the first prism sub-sheet 171 and the second prism sub-sheet 172, causing the ultraviolet light to be emitted in a specific direction, to implement the best disinfection effect.

Arrangements of the first prism sub-sheet 171 and the second prism sub-sheet 172 may also converge the ultraviolet light emitted from the light-transmitting opening 1131. Specifically, when the first prism sub-sheet 171 and the second prism sub-sheet 172 are not arranged, the ultraviolet light emitted from the light-transmitting opening 1131 is diffused. When the second light-emitting unit 15 is arranged close to two end sides that are of the back plate 11 and that are opposite to each other, that is, the back plate 11 is close to an end side of the cover plate 18 and an end side of the cover plate 18 away from the back plate 11, the ultraviolet light emitted by the second light-emitting unit 15 is easy to be emitted from the display device 10. When the first prism sub-sheet 171 and the second prism sub-sheet 172 are arranged, the ultraviolet light emitted by the light-transmitting opening 1131 are converged by the first prism sub-sheet 171 and the second prism sub-sheet 172. In addition, when the first prism sub-sheet 171 is a prism sheet with a specification of 0°, and the second prism sub-sheet 172 is a prism sheet with a specification of 90°, an emitting range of the ultraviolet light in the air changes from an approximate inverse cone to an approximate cube, so that a situation in which the ultraviolet light leaks from a side of the display device 10 is reduced. This protects physical and mental health of a user of the display device 10 while improving the use efficiency of the ultraviolet light.

Refer to FIG. 3. The plane on which the light-transmitting opening 1131 is located is away from a plane on which the transparent cover plate 122 is located by a distance $H_1$. The distance $H_1$ satisfies: 0.3 mm≤$H_1$≤0.5 mm.

The distance $H_1$ may be a distance between a location of a central point of the plane on which the light-transmitting opening 1131 is located and the plane on which the transparent cover plate 122. The distance $H_1$ may be, but is not limited to, 0.3 mm, 0.4 mm, 0.5 mm, or the like. It can be understood that the distance $H_1$ may alternatively be another value, provided that 0.3 mm≤$H_1$≤0.5 mm. The distance $H_1$ satisfies 0.3 mm≤$H_1$≤0.5 mm, so that the ultraviolet light emitted by the second light-emitting unit 15 covers a larger area on the display panel 12, and a cleaning efficiency of the ultraviolet light emitted by the second light-emitting unit 15 for the display panel 12.

Figure 21:
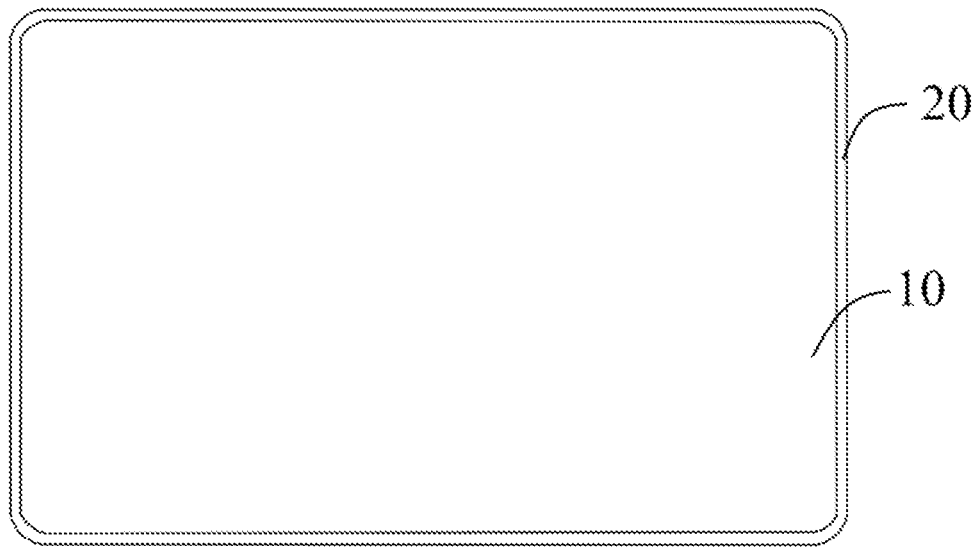
FIG. 21 is a schematic structural diagram of an electronic device in an implementation of the present disclosure.
Figure 22:
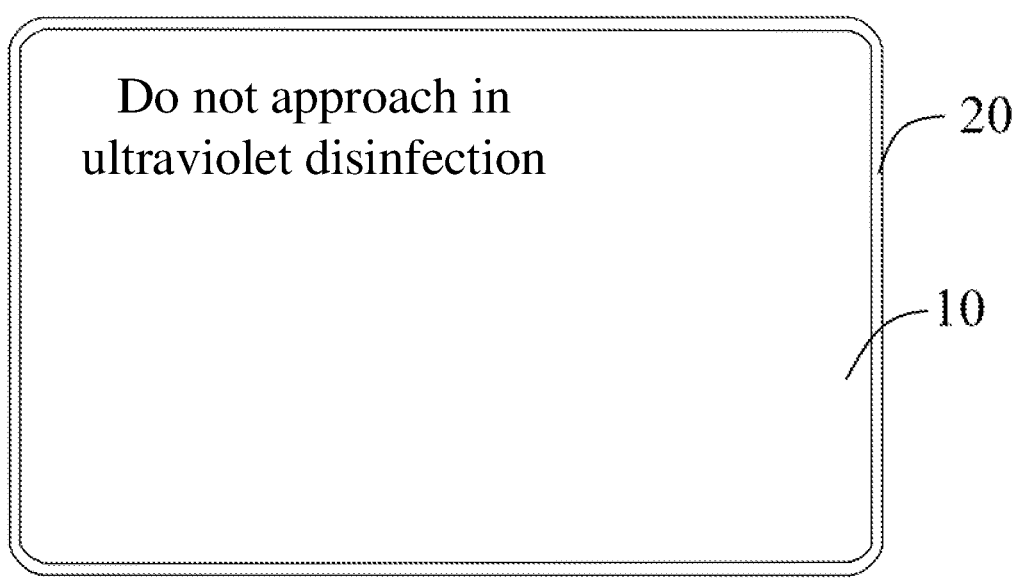
FIG. 22 is a schematic structural diagram of an electronic device in an implementation of the present disclosure.

Refer to FIG. 21 and FIG. 22. FIG. 21 is a schematic structural diagram of an electronic device in an implementation of the present disclosure, and FIG. 22 is a schematic structural diagram of an electronic device in an implementation of the present disclosure. An electronic device 1 is further provided in the present disclosure. The electronic device 1 includes a housing 20 and the display device 10. The housing 20 is configured to accommodate the display device 10.

The electronic device 1 may be, but is not limited to, automatic ticket machines of the train and subway, machine control machines, in-vehicle displays, or the like. The electronic device 1 may alternatively be a device with a display function, such as a smartphone, a portable phone, a navigation device, a Television (TV), an in-vehicle speaker body, a laptop computer, a tablet computer, a Portable Media Player (PMP), or a Personal Digital Assistant (PDA).

The electronic device 1 provided in this implementation includes the display device 10. The display device 10 provided in this implementation cleans the display panel 12 by using the ultraviolet light emitted by the second light-emitting unit 15, and may cancel disinfection of the display device 10 in a manner of manual spraying and wiping, to reduce costs of manpower and materials. In addition, the display device 10 disinfects in a manner of self-emitting ultraviolet light, which has low costs, simple operation, short disinfection time, and high efficiency. The ultraviolet light emitted by the second light-emitting unit 15 provided in this implementation at least partially avoids the optical film 13, and can be directly emitted via the transparent cover plate 122 of the display panel 12, to reduce waste and loss of the ultraviolet light, so that the display panel 12 receives the ultraviolet light to a greater extent and use efficiency of the ultraviolet light is improved, to fully clean and disinfect the display panel 12. The ultraviolet light emitted by the second light-emitting unit 15 can not only disinfect the surface of the display panel 12, but also clean air around the display device 10, to effectively protect health of a user of the display device 10.

In an implementation of the present disclosure, because ultraviolet light is invisible light, to prevent the user from contact for long and affecting physical and mental health, the display device 10 can turn on visible light while being switched on, and a picture needs to display a prompt "Do not approach in ultraviolet disinfection".

In an implementation of the present disclosure, during ultraviolet light disinfection, to prevent a residue on a picture from affecting product functions, the picture of the display device 10 may be set to a rolling switch function.

The electronic device 1 may further include a sensor, a control chip, and the like. The sensor is configured to collect a dirtiness situation of a display panel of the display device 10 and obtain a feedback signal. The control chip is configured to receive the feedback signal and optionally turn on the second light-emitting unit 15. The second light-emitting unit 15 emits the ultraviolet light to the display panel 12 to clean the display panel 12 during turning on. A collecting manner of the sensor may be, but is not limited to, collecting fingerprint press on a screen of the display device 10, detecting a block of a screen, or the like, to intelligently select turning on the second light-emitting unit 15, so that the electronic device 1 uses a principle of ultraviolet light disinfection to implement self-disinfection, breaking through a concept of disinfection by manually spraying and swiping. This can not only effectively achieve an object, but also reduce manpower and materials with low costs, and implementability is high.

The term "embodiment" or "implementation" referred to herein means that particular features, structures, or characteristics described in conjunction with implementations may be defined in at least one implementation of the present disclosure. The phrase "implementation" appearing in various places in the specification does not necessarily refer to the same implementation or an independent or alternative implementation that is mutually exclusive with other implementations. Those skilled in the art will understand expressly and implicitly that an implementation described herein may be combined with other implementations. In addition, it should also be understood that the features, structures, or characteristics described in implementations of the present disclosure may be arbitrarily combined without contradiction, so as to form another implementation without departing from the spirit and scope of technical solutions of the present disclosure.

Finally, it should be noted that the above implementations are only used to illustrate the technical solutions of the present disclosure rather than limit. Although the present disclosure is illustrated in detail with reference to the above preferred implementations, those of ordinary skill in the art should understand that, any modification or equivalent replacement of the technical solutions of the present disclosure should not depart from the spirit and scope of the technical solutions of the present disclosure.

What is claimed is:

1. A display device, comprising:
    a back plate comprising a body portion and a carrier portion, wherein the carrier portion is connected to a periphery of the body portion in a bent manner, the carrier portion comprises a first sub-carrier portion and a second sub-carrier portion, the second sub-carrier portion is closer to an outer periphery of the back plate than the first sub-carrier portion, the second sub-carrier portion is farther away from the body portion than the first sub-carrier portion;
    a display panel, wherein the display panel is carried on the back plate, the display panel and the back plate cooperatively define an accommodating cavity, the display panel comprises a display screen and a transparent cover plate, the display screen is carried on the second sub-carrier portion, the transparent cover plate is carried on the second sub-carrier portion, and the transparent cover plate is farther away from the body portion than the display screen;
    an optical film, wherein the optical film is accommodated in the accommodating cavity;
    a first light-emitting unit, wherein the first light-emitting unit is accommodated in the accommodating cavity and located on one side of the optical film away from the display panel, the first light-emitting unit is configured to emit visible light, and the visible light emitted by the first light-emitting unit is incident on the display panel via the optical film; and
    a second light-emitting unit, wherein the second light-emitting unit is carried on the second sub-carrier portion of the back plate, the second light-emitting unit is configured to emit ultraviolet light, a part of the ultraviolet light emitted by the second light-emitting unit avoids the display screen and is emitted onto the transparent cover plate, and another part of the ultraviolet light emitted by the second light-emitting unit is emitted onto the transparent cover plate via the display screen, to clean the display panel.

2. The display device of claim 1, wherein
    the first sub-carrier portion is configured to carry the optical film, the second sub-carrier portion is configured to carry the display panel, the second sub-carrier portion defines an accommodating groove, and the second light-emitting unit is accommodated in the second accommodating groove.

3. The display device of claim 2, wherein the accommodating groove has a light-transmitting opening for the ultraviolet light to pass through, and a plane on which the light-transmitting opening is located and a plane on which the display panel is located defines an angle a therebetween, and the angle a satisfies: $15° \leq a \leq 30°$.

4. The display device of claim 3, wherein the second sub-carrier portion has:
    a first carrier surface, wherein the first carrier surface is configured to carry the display screen;
    a connecting surface, wherein the connecting surface is connected to the first carrier surface in a bent manner, the connecting surface is inclined relative to the first carrier surface, the connecting surface defines the light-transmitting opening, and an orthographic projection of the transparent cover plate on the back plate covers the light-transmitting opening; and
    a second carrier surface, wherein the second carrier surface is connected to the connecting surface in a bent manner, the second carrier surface is closer to the outer periphery of the back plate than the first carrier surface, the second carrier surface is farther away from the body portion than the first carrier surface, and the second carrier surface is configured to carry the transparent cover plate.

5. The display device of claim 3, wherein the display device further comprises a prism sheet, the prism sheet is configured to cover the light-transmitting opening, the prism sheet comprises a first prism sub-sheet and a second prism sub-sheet, the first prism sub-sheet and the second prism sub-sheet are arranged in a stacked manner, the display device has a first direction and a second direction, the first prism sub-sheet comprises a first base and a first prism column, the first prism column is carried on the first base and extends in the first direction, the second prism sub-sheet comprises a second base and a second prism column, and the second prism column is carried on the second base and extends in the second direction, wherein the first direction is orthogonal to the second direction.

6. The display device of claim 3, wherein the plane on which the light-transmitting opening is located is away from a plane on which the transparent cover plate is located by a distance $H_1$, and the distance $H_1$ satisfies: $0.3 \text{ mm} \leq H_1 \leq 0.5 \text{ mm}$.

7. The display device of claim 2, wherein the accommodating groove comprises:
    a first accommodating sub-groove, wherein the second light-emitting unit is accommodated in the first accommodating sub-groove; and
    a second accommodating sub-groove, wherein the second accommodating sub-groove has a receiving opening and a light-transmitting opening opposite to the receiving opening, the receiving opening of the second accommodating sub-groove communicates with the first accommodating sub-groove, and the light-transmitting opening of the second accommodating sub-groove is exposed beyond the second sub-carrier portion, wherein
    the second light-emitting unit has a size $D_1$ in a transverse direction, and the receiving opening has a size $D_2$ in the transverse direction, wherein the size $D_1$ and the size $D_2$ satisfies: $D_1 \leq D_2$.

8. The display device of claim 7, wherein the second accommodating sub-groove comprises:

a first portion, wherein the first portion is arranged close to the second light-emitting unit, and one end of the first portion close to the second light-emitting unit defines the receiving opening;

a second portion, wherein the second portion is arranged at one end of the first portion away from the second accommodating sub-groove, the second portion communicates with the first portion, the second portion has a first opening and a second opening opposite to the first opening, the first opening has a size $D_3$ in the transverse direction, and the second opening has a size $D_4$ in the transverse direction; and a third portion, wherein the third portion is arranged at one end of the second portion away from the first portion, one end of the third portion communicates with the second portion, another end of the third portion has the light-transmitting opening, and the light-transmitting opening has a size $D_5$, wherein the size $D_2$ of the receiving opening and the size $D_3$ of the first opening satisfies: $D_2 \geq D_3$, and the size $D_4$ of the second opening and the size $D_5$ of the light-transmitting opening satisfies: $D_4 \leq D_5$.

9. An electronic device, comprising a housing and a display device, wherein the display device comprises:

a back plate comprising a body portion and a carrier portion, wherein the carrier portion is connected to a periphery of the body portion in a bent manner, the carrier portion comprises a first sub-carrier portion and a second sub-carrier portion, the second sub-carrier portion is closer to an outer periphery of the back plate than the first sub-carrier portion, the second sub-carrier portion is farther away from the body portion than the first sub-carrier portion;

a display panel, wherein the display panel is carried on the back plate, the display panel and the back plate cooperatively define an accommodating cavity, the display panel comprises a display screen and a transparent cover plate, the display screen is carried on the second sub-carrier portion, the transparent cover plate is carried on the second sub-carrier portion, and the transparent cover plate is farther away from the body portion than the display screen;

an optical film, wherein the optical film is accommodated in the accommodating cavity;

a first light-emitting unit, wherein the first light-emitting unit is accommodated in the accommodating cavity and located on one side of the optical film away from the display panel, the first light-emitting unit is configured to emit visible light, and the visible light emitted by the first light-emitting unit is incident on the display panel via the optical film; and a second light-emitting unit, wherein the second light-emitting unit is carried on the second sub-carrier portion of the back plate, the second light-emitting unit is configured to emit ultraviolet light, a part of the ultraviolet light emitted by the second light-emitting unit avoids the display screen and is emitted onto the transparent cover plate, and another part of the ultraviolet light emitted by the second light-emitting unit is emitted onto the transparent cover plate via the display screen, to clean the display panel, wherein the housing is configured to accommodate the display device.

10. The electronic device of claim 9, wherein the first sub-carrier portion is configured to carry the optical film, the second sub-carrier portion is configured to carry the display panel, the second sub-carrier portion defines an accommodating groove, and the second light-emitting unit is accommodated in the second accommodating groove.

11. The electronic device of claim 10, wherein the accommodating groove has a light-transmitting opening for the ultraviolet light to pass through, and a plane on which the light-transmitting opening is located and a plane on which the display panel is located defines an angle a therebetween, and the angle a satisfies: $15° \leq a \leq 30°$.

12. The electronic device of claim 11, wherein the second sub-carrier portion has:

a first carrier surface, wherein the first carrier surface is configured to carry the display screen;

a connecting surface, wherein the connecting surface is connected to the first carrier surface in a bent manner, the connecting surface is inclined relative to the first carrier surface, the connecting surface defines the light-transmitting opening, and an orthographic projection of the transparent cover plate on the back plate covers the light-transmitting opening; and a second carrier surface, wherein the second carrier surface is connected to the connecting surface in a bent manner, the second carrier surface is closer to the outer periphery of the back plate than the first carrier surface, the second carrier surface is farther away from the body portion than the first carrier surface, and the second carrier surface is configured to carry the transparent cover plate.

13. The electronic device of claim 11, wherein the display device further comprises a prism sheet, the prism sheet is configured to cover the light-transmitting opening, the prism sheet comprises a first prism sub-sheet and a second prism sub-sheet, the first prism sub-sheet and the second prism sub-sheet are arranged in a stacked manner, the display device has a first direction and a second direction, the first prism sub-sheet comprises a first base and a first prism column, the first prism column is carried on the first base and extends in the first direction, the second prism sub-sheet comprises a second base and a second prism column, and the second prism column is carried on the second base and extends in the second direction, wherein the first direction is orthogonal to the second direction.

14. The electronic device of claim 11, wherein the plane on which the light-transmitting opening is located is away from a plane on which the transparent cover plate is located by a distance $H_1$, and the distance $H_1$ satisfies: $0.3 \text{ mm} \leq H_1 \leq 0.5 \text{ mm}$.

15. The electronic device of claim 10, wherein the accommodating groove comprises:

a first accommodating sub-groove, wherein the second light-emitting unit is accommodated in the first accommodating sub-groove; and a second accommodating sub-groove, wherein the second accommodating sub-groove has a receiving opening and a light-transmitting opening opposite to the receiving opening, the receiving opening of the second accommodating sub-groove communicates with the first accommodating sub-groove, and the light-transmitting opening of the second accommodating sub-groove is exposed beyond the second sub-carrier portion, wherein the second light-emitting unit has a size $D_1$ in a transverse direction, and the receiving opening has a size $D_2$ in the transverse direction, wherein the size $D_1$ and the size $D_2$ satisfies: $D_1 \leq D_2$.

16. The electronic device of claim 15, wherein the second accommodating sub-groove comprises:

a first portion, wherein the first portion is arranged close to the second light-emitting unit, and one end of the first portion close to the second light-emitting unit defines the receiving opening;

a second portion, wherein the second portion is arranged at one end of the first portion away from the second accommodating sub-groove, the second portion communicates with the first portion, the second portion has a first opening and a second opening opposite to the first opening, the first opening has a size $D_3$ in the transverse direction, and the second opening has a size $D_4$ in the transverse direction; and a third portion, wherein the third portion is arranged at one end of the second portion away from the first portion, one end of the third portion communicates with the second portion, another end of the third portion has the light-transmitting opening, and the light-transmitting opening has a size $D_5$, wherein the size $D_2$ of the receiving opening and the size $D_3$ of the first opening satisfies: $D_2 \geq D_3$, and the size $D_4$ of the second opening and the size $D_5$ of the light-transmitting opening satisfies: $D_4 \leq D_5$.

\* \* \* \* \*